United States Patent [19]

Koga et al.

[11] 4,212,828
[45] Jul. 15, 1980

[54] NOVEL PROCESS FOR ASYMMETRIC SYNTHESIS OF OPTICALLY ACTIVE 2-ALKANOYL-1,2,3,4-TETRAHYDRO-2-NAPHTHOL COMPOUNDS

[75] Inventors: Kenji Koga; Shiro Terashima, both of Tokyo, Japan

[73] Assignee: Sumitomo Chemical Company, Limited, Osaka, Japan

[21] Appl. No.: 963,174

[22] Filed: Nov. 24, 1978

[30] Foreign Application Priority Data

Apr. 14, 1978 [JP] Japan .................................. 53-44388

[51] Int. Cl.$^2$ ........................ C07C 45/00; C07C 65/14
[52] U.S. Cl. .................................... 568/314; 562/467; 260/326.33; 568/319
[58] Field of Search ................... 540/590 R; 562/467, 562/471, 501, 508; 260/590 R, 590 O

[56] References Cited

PUBLICATIONS

Koga et al., Tetrahedron Letters, 1977, pp. 3532–3537 (1977).

Primary Examiner—Norman Morgenstern
Assistant Examiner—James H. Reamer
Attorney, Agent, or Firm—Birch, Stewart, Kolasch and Birch

[57] ABSTRACT

A process for asymmetric synthesis of optically active 2-alkanoyl-1,2,3,4-tetrahydro-2-naphthol compounds of the formula:

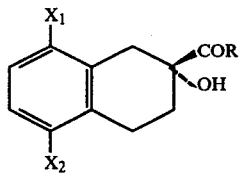

from L-proline or its ester and the following carboxylic acid of the formula:

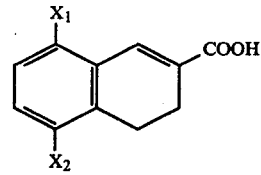

or its reactive derivative through the following intermediary compounds in order:

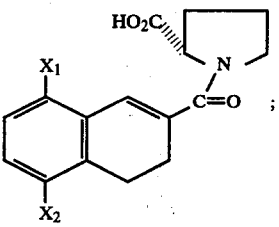

and

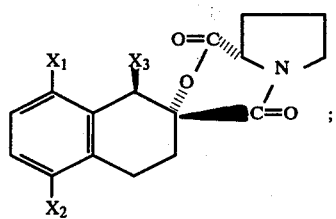

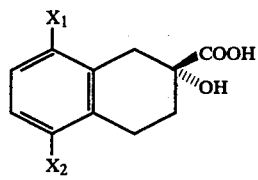

1 Claim, No Drawings.

NOVEL PROCESS FOR ASYMMETRIC SYNTHESIS OF OPTICALLY ACTIVE 2-ALKANOYL-1,2,3,4-TETRAHYDRO-2-NAPHTHOL COMPOUNDS

The present invention relates to a novel process for asymmetric synthesis of optically active 2-alkanoyl-1,2,3,4-tetrahydro-2-naphthol compounds representable by the formula (I):

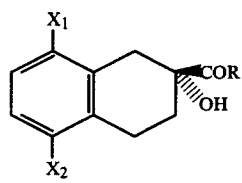
(I)

wherein $X_1$ and $X_2$ are each a hydrogen atom or a lower alkoxy group and R is a lower alkyl group.

The comounds (I) are extremely useful as starting materials for synthesis of anthracycline antibiotics such as adriamycin (1) and daunorubicin (2) which have recently attracted much attention because of their notable antineoplastic activities [Lloydia, 40, 45 (1977)].

From dl-2-acetyl-5,8-dimethoxy-1,2,3,4-tetrahydro-2-naphthol [(I), $X_1$, $X_2$=—$OCH_3$; R=—$CH_3$), for example, racemic daunomycin (4), the aglycone of (2), is synthesized [Can. J. Chem., 49, 2712 (1971); ibid. 51, 466 (1973)].

Further, synthesis of adriamycinone (3), the aglycone of (1), from (4) has been also reported [J. Am. Chem. Soc., 98, 1969 (1976); J. Med. Chem., 17, 659 (1974)].

It is known that (1) and (2) may sometimes cause cardiac lesions as the secondary effect when used in large amounts. As non-natural anthracyclines hardly producing undesirable secondary effects such as cardiac lesions, 4-demethoxy-adriamycin (5) and 4-demethoxy-daunorubicin (6) have been developed [Tetrahedron Letters, 1977, 3537; Cancer Treat. Rep., 60, 829 (1976); German Offen. No. 2601785; Lloydia, 40, 45 (1977)]. They are considered to have more excellent pharmacological activities than those of (1) and (2). For the synthesis of these optically active compounds (5) and (6), optically active (R)(-)-2-acetyl-5,8-dimethoxy-1,2,3,4-tetrahydro-2-naphthol [(I), $X_1$, $X_2$=—$OCH_3$; R=—$CH_3$] is used as the starting material.

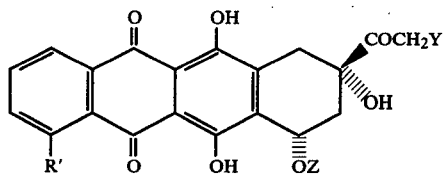

| | R' | Y | Z |
|---|---|---|---|
| (1) | $OCH_3$ | OH | 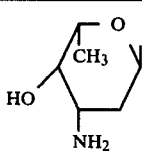 |
| (2) | $OCH_3$ | H | 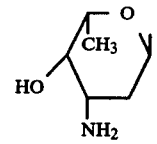 |
| (3) | $OCH_3$ | OH | H |
| (4) | $OCH_3$ | H | H |
| (5) | H | OH | 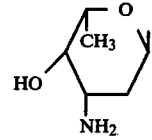 |
| (6) | H | H | 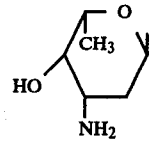 |

As mentioned above, the optically active compounds (I) are of great importance as starting materials for synthesis of natural and non-natural anthracyclines in optically active form. For preparation of the compounds (I), however, only an optical resolution procedure is attempted in which a racemic product [(I), $X_1$, $X_2$=—$OCH_3$; R=—$CH_3$] produced from 2,5-dimethoxybenzaldehyde by way of the seven steps [Can. J. Chem., 49, 2712 (1971)] or the nine steps [Can. J. Chem., 51, 466 (1973)] is subjected to optical resolution in the presence of optically active α-phenylethylamine [German. Offen. No. 2601785].

The present inventors have succeeded in developing a process for asymmetric synthesis of the compounds (I) having an extremely high optical purity by treating L-proline or its ester which is readily available with an α,β-unsaturated carboxylic acid represented by the formula (II):

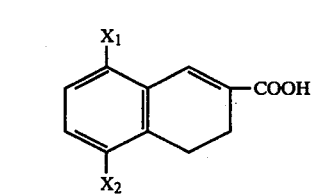
(II)

wherein $X_1$ and $X_2$ are each as defined above or a reactive derivative thereof to obtain an N-(α,β-unsaturated acyl)-L-proline derivative represented by the formula (III):

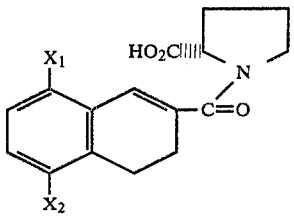

(III)

wherein $X_1$ and $X_2$ are each as defined above, subjecting the thus obtained product to an asymmetric halolactonization reaction to obtain an optically active halolactone represented by the formula (IV):

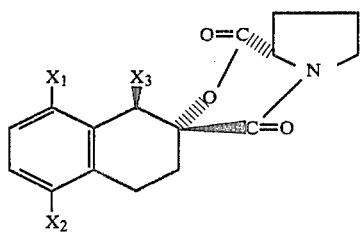

(IV)

wherein $X_1$ and $X_2$ are each as defined above and $X_3$ is a halogen atom, subjecting the thus obtained product to dehalogenation and subsequent hydrolysis to obtain an optically active 2-hydroxy-1,2,3,4-tetrahydro-2-naphthoic acid compound represented by the formula (V):

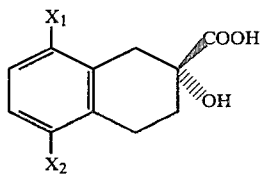

(V)

wherein $X_1$ and $X_2$ are each as defined above and then treating the thus obtained product with an alkyl metal compound to obtain the compound (I).

The process for preparation of the optically active compounds (I) according to the invention will be hereinafter explained in detail.

The reaction between L-proline or its ester and the α,β-unsaturated carboxylic acid (II) is usually effected by condensing an ester such as ethyl L-prolinate in the presence of diethylphosphorocyanidate (hereinafter referred to as "DEPC") to obtain an ester of the compound (III) and then subjecting the ester to hydrolysis in the presence of potassium hydroxide or the like to obtain the compound (III).

The asymmetric lactonization of the compound (III) into the compound (IV) is usually carried out under conventional conditions for halolactonization. As the halogenating agent to be used, N-bromosuccinimide is exemplified.

The halogenating agent is used in an optional amount not smaller than 1 mol equivalent, preferably 1 to 3 mol equivalent. If necessary, an inorganic base such as an alkali metal alkoxide (e.g. potassium t-butoxide) may be used in combination with the halogenating agent.

The reaction is favorably carried out in a solvent. Particularly preferred examples of the solvent to be used are dimethylformamide (DMF), chloroform, carbon tetrachloride and dichloromethane which are inert to the halogenating agent.

The reaction temperature may be decided optionally. In the usual case, a temperature from −20° C. to room temperature is adopted.

In the case that $X_1$ and $X_2$ are both a hydrogen atom and $X_3$ is a bromine atom (7a) and in the case that $X_1$ and $X_2$ are both —$OCH_3$ groups and $X_3$ is a bromine atom (7b), the formed optically active halolactone (IV) comprises the two kinds of diastereomers as shown below. The proportion of these diastereomers is as follows: 7aA:7aB=96:4 in (7a); 7bA:7bB=98.5:1.5 in the (7b), as shown in below-mentioned working examples. Thus, in both cases, one of the stereo-isomers is formed with extreme predominance.

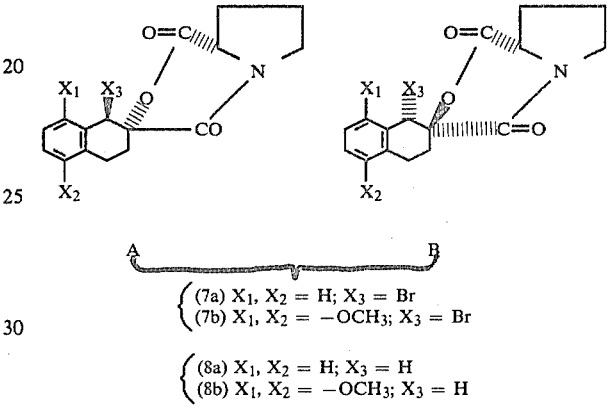

$\begin{cases} (7a) \ X_1, X_2 = H; X_3 = Br \\ (7b) \ X_1, X_2 = -OCH_3; X_3 = Br \end{cases}$ $\begin{cases} (8a) \ X_1, X_2 = H; X_3 = H \\ (8b) \ X_1, X_2 = -OCH_3; X_3 = H \end{cases}$ The dehalogenation reaction can be effected easily and efficiently by reduction with trialkyltin hydride.

In the reaction, the presence of a solvent is not necessarily required, but an inert solvent such as benzene, toluene or bromobenzene is usually employed.

A catalytic amount of azobisisobutyronitrile (AIBN) is also incorporated into the reaction system.

The reaction temperature may be optionally selected from a wide range of temperatures. In the usual case, a temperature from room temperature to 200° C. is adopted.

Thus, the lactone derivative (IV) in which $X_3$ is a hydrogen atom can be obtained.

The hydrolysis reaction may be effected under conventional conditions, for example, under an acidic condition in the presence of hydrochloric acid.

The reaction is carried out in an aqueous solvent such as water or a mixture of water and a water-miscible organic solvent (e.g. methanol, ethanol).

When the reaction is carried out in the presence of an alcoholic solvent such as methanol, partial formation of an ester such as the methyl ester may be sometimes observed simultaneously with hydrolysis of the lactone portion. In such case, the product is subjected to hydrolysis, especially under an alkaline condition, so as to obtain the objective hydroxy-carboxylic acid (V).

The reaction between the compound (V) and the alkyl metal compound may be effected under conventional conditions for reaction of alkyl metal compounds. As the reaction solvent to be advantageously used, ether and tetrahydrofuran are exemplified. The reaction temperature is usually room temperature, but if necessary, heating or cooling may be effected so as to regulate the progress of the reaction.

As the alkyl metal compound to be used, alkyl lithium compounds such as methyl lithium are exemplified.

According to the above mentioned process of the invention, the optically active compound (I) can be readily obtained, for example, with an optical purity of 92% to 100%, as shown in the below-mentioned working examples.

Practical and presently preferred embodiments of the invention are illustratively shown in the following Examples which are schematically summarized as shown below:

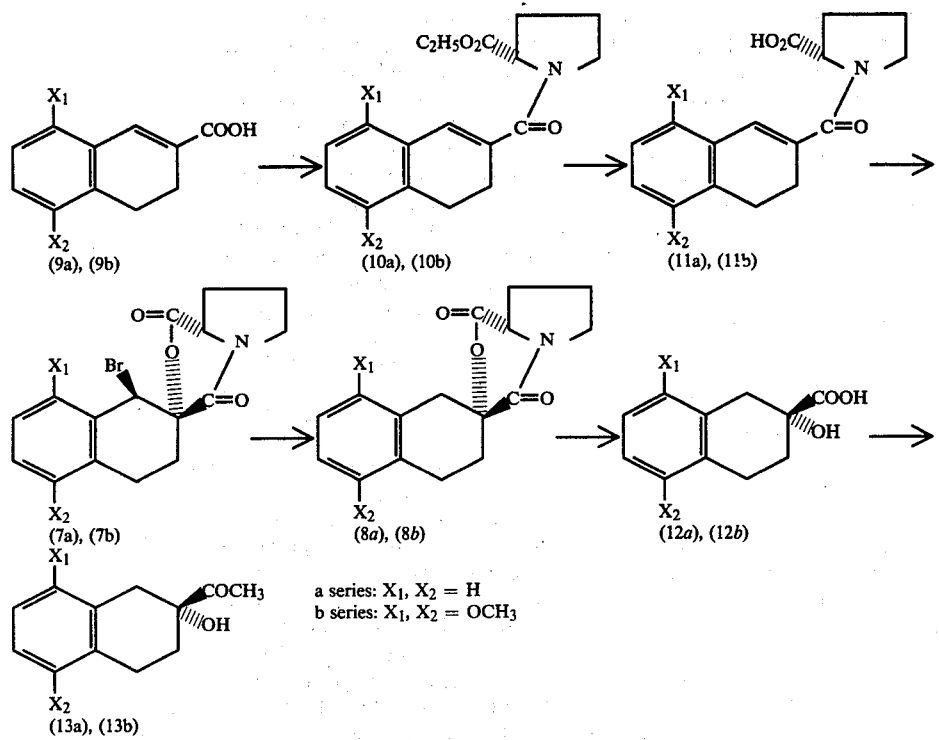

a series: $X_1, X_2 = H$
b series: $X_1, X_2 = OCH_3$

EXAMPLE 1

(S)(−)-Ethyl N-(3,4-dihydro-2-naphthoyl)prolinate (10a)

To a DMF solution (60 ml) containing 3,4-dihydro-2-naphthoic acid (9a, 7.12 g, 40.0 mmole), and (S)(−)-ethyl prolinate (6.41 g, 44.8 mmole), a DMF solution (60 ml) containing DEPC (7.17 g, 44.0 mmole) and a DMF solution (60 ml) containing triethylamine (4.05 g, 40.0 mmole) are dropwise added at 0° C. in 5 minutes. The resultant mixture is stirred at 0° C. for 2 hours and then at room temperature for 2 days. The reaction mixture is diluted with ethyl acetate (1.8 liters), and the ethyl acetate solution is washed with 5% hydrochloric acid (130 ml×2), water (130 ml×2), a saturated aqueous solution of sodium chloride (130 ml×2), a saturated aqueous solution of sodium hydrogen carbonate (130 ml×2) and water (130 ml×2) in order and then dried over anhydrous magnesium sulfate. After filtration and evaporation, a crude product (10a) is obtained as a yellow caramel (13.9 g, 116%), which is purified by column chromatography (silica gel, 300 g; solvent, ether) to obtain an almost pure product (10a) as colorless needles (11.1 g, 91%). M.P. 55°–57° C. Recrystallization from ether-hexane affords an analytical sample as colorless needles melting at 56°–57° C. $[\alpha]_D^{20} -18.6°$ (c=1.03, ethanol). IR$\nu_{max}^{Nujol}$ cm$^{-1}$: 1750 (ester), 1650 (C=C), 1610 (CON), NMR (in CDCl$_3$): 1.27 (3H, t, J=7 Hz, CO$_2$CH$_2$C$\underline{H}_3$), 1.64–2.40 (4H, m, NCH$_2$C$\underline{H}_2$C$\underline{H}_2$), 2.40–3.20 (4H, m, C$\underline{H}_2$C$\underline{H}_2$C=), 3.72 (2H, t, J=6 Hz, N—C$\underline{H}_2$), 4.16 (2H, q, J=7 Hz, CO$_2$C$\underline{H}_2$CH$_3$), 4.58 (1H, t, J=6 Hz, NC$\underline{H}$CO$_2$), 6.77 (1H, s, C$\underline{H}$=C), 7.12 (4H, s, aromatic proton).

Elementary analysis: Calcd. for C$_{18}$H$_{21}$O$_3$N: C, 72.22; H, 7.07; N, 4.68. Found: C, 72.22; H, 7.02; N, 4.72.

(S) (−)-N-(3,4-Dihydro-2-naphthoyl)proline (11a)

To a 50% aqueous ethanol solution (100 ml) containing potassium hydroxide (2.56 g, 0.039 mmole), (10a) (9.09 g, 0.030 mole) is added, and the mixture is stirred at room temperature for 5 hours. After completion of the reaction, the reaction mixture is concentrated to the one-fourth of the amount under reduced pressure, and the resultant aqueous alkaline solution is washed with ether (50 ml×2). The aqueous alkaline layer is adjusted to about pH 2 with conc. hydrochloric acid, and the precipitated product is extracted with ethyl acetate (150 ml×2). The ethyl acetate layers are combined, washed with a saturated aqueous solution of sodium chloride (30 ml×2) and dried over anhydrous magnesium sulfate. After filtration and evaporation, a pure product (11a) is obtained as a colorless caramel (8.1 g, 98%). $[\alpha]_D^{20} -93.3°$ (c=2.16, chloroform). IR$\nu_{max}^{Nujol}$ cm$^{-1}$: 1730 (COOH), 1630 (C=C), 1570 (CON). NMR (in CDCl$_3$): 1.73–2.43 (4H, m, NCH$_2$C$\underline{H}_2$CH$_2$), 2.43–3.15 (4H, m, C$\underline{H}_2$C$\underline{H}_2$C=), 3.69 (2H, t, J=6Hz, NC$\underline{H}_2$), 4.60 (1H, t, J=7H$_z$, NC$\underline{H}$CO$_2$), 6.75 (1H, s, C$\underline{H}$=C), 7.09 (4H, s, aromatic proton), 8.65 (COOH).

Asymmetric bromolactonization of (S) (−)-N-(3,4-dihydro-2-naphthoyl)proline

To a DMF solution (15 ml) of (11a) (4.57 g, 16.9 mmole), a DMF solution (45 ml) of potassium t-butoxide (1.89 g, 16.9 mmole) and a DMF solution (15 ml) of NBS (6.00 g, 33.7 mmole) are added at −20° C. in a nitrogen stream. The resultant mixture is stirred at −20° C. for 2 hours and then at room temperature for 20 hours. Then, the reaction mixture is diluted with ethyl acetate (800 ml), and the ethyl acetate solution is washed with a 5% aqueous solution of sodium hydrogen carbonate (150 ml×6), water (150 ml×4) and a saturated aqueous solution of sodium chloride (150 ml×2) in order and dried over anhydrous magnesium sulfate. After filtration and evaporation, a crude product (7a) (mixture of 7aA and 7aB) is obtained as yellow needles (4.64 g, 79%). M.P. 166°–170° C. $[\alpha]_D^{20}$ −68.6° (c=1.01, chloroform). The proportion of the two kinds of diastereomers (7aA and 7aB) contained in the crude 7a is presumed to be 96:4 on the basis of the fact that 12a having an optical purity of 92% is obtained therefrom and in view of the reaction mechanism in the asymmetric bromolactonization which has already been studied in detail (Tetrahedron Letters, 1977, 1005; Chemistry Letters, 1977, 1109). Recrystallization of the crude 7a from ether-hexane affords the predominant 7aA as the single product in colorless needle form. M.P. 196°–197° C. $[\alpha]_D^{20}$ −88.8° (c=1.02, chloroform). IR$\nu_{max}^{Nujol}$ cm$^{-1}$: 1760 (lactone), 1683 (CON). NMR (in CDCl$_3$): 1.60–2.70 (4H, m, NCH$_2$C$\underline{H}_2$CH$_2$), 2.70–3.40 (4H, m, C$\underline{H}_2$C$\underline{H}_2$CCHBr), 4.30–4.80 (2H, m, N—C$\underline{H}_2$), 5.31 (1H, d, J=3H$_z$, C$\underline{H}$Br), 6.97–7.27 (4H, m, aromatic proton).

Elementary analysis: Calcd. for C$_{16}$H$_{16}$NO$_3$Br: C, 54.87; H, 4.61; N, 4.00. Found: C, 54.62; H, 4.61; N, 3.89.

Debromination of the bromolactone (7a)

To a bromobenzene solution (74 ml) containing the crude 7a (mixture of 7aA and 7aB) (M.P. 166°–170° C.; $[\alpha]_D^{20}$ −68.6° (c=1.01, chloroform)) (4.0 g, 11.4 mmole), a bromobenzene solution (18.5 ml) containing tri-n-butyltin hydride (13.3 g, 45.7 mmole) is added, and the resultant mixture is stirred at about 65° C. for 9 hours in an argon stream while adding a bromobenzene solution (5 ml) of AIBN (31.3 mg) every 3 hours. The reaction mixture is concentrated under reduced pressure (10 mmHg; bath temperature, 60° C. or lower) to evaporate bromobenzene. The residue is purified by column chromatography (silica gel, 350 g; solvent, hexane and then hexane-ether (2:1)) to obtain a crude product 8a (mixture of 8aA and 8aB) as pale yellow needles (2.34 g, 76%). M.P. 165°–173° C. $[\alpha]_D^{20}$ −156° (c=0.502, chloroform).

The same reaction is repeated using the single product 7aA (M.P. 196°–197° C.; $[\alpha]_D^{20}$ −88.8° (c=1.02, chloroform) (1.10 g, 3.14 mmole). After the purification by column chromatography, the product 8aA is obtained as colorless needles with a yield of 79%. M.P. 166°–173° C. $[\alpha]_D^{20}$ −151° (c=0.531, chloroform). Recrystallization from ether-chloroform affords an analytical sample of 8aA as colorless needles. M.P. 173°–175° C. $[\alpha]_D^{20}$ −154° (c=0.500, chloroform). IR$\nu_{max}^{Nujol}$ cm$^{-1}$: 1758 (lactone), 1662 (CON). NMR (in CDCl$_3$): 1.88–2.55 (6H, m, NCH$_2$C$\underline{H}_2$C$\underline{H}_2$ and CH$_2$C$\underline{H}_2$CCH$_2$), 2.55–3.05 (2H, m, C$\underline{H}_2$CH$_2$CCH$_2$), 3.20 (2H, broad s, CH$_2$CH$_2$CC$\underline{H}_2$), 3.40–3.90 (2H, m, NC$\underline{H}_2$), 4.35 (1H, broad t, J=9.6H$_z$, NC$\underline{H}$CO$_2$), 7.05 (4H, m, aromatic proton).

Elementary analysis: Calcd. for C$_{16}$H$_{17}$NO$_3$.1/5H$_2$O: C, 69.96; H, 6.38; N, 5.09. Found: C, 69.96; H, 6.19; N, 5.21.

(R) (−)-2-Hydroxy-1,2,3,4-tetrahydro-2-naphthoic acid (12a)

The crude product 8a (mixture of 8aA and 8aB) (M.P. 165°–173° C., $[\alpha]_D^{20}$ −156° (c=0.502, chloroform)) (1.50 g, 5.53 mmole) is added to 36% conc. hydrochloric acid (50 ml), and the mixture is stirred for 3 hours under boiling. The reaction mixture is saturated with sodium chloride and extracted with ethyl acetate (50 ml×3). The ethyl acetate layers are combined and extracted with a saturated aqueous solution of sodium hydrogen carbonate (100 ml×2). The aqueous sodium hydrogen carbonate solutions obtained by the extraction are combined, adjusted to about pH 2 with conc. hydrochloric acid and, after saturation with sodium chloride, extracted with ethyl acetate (100 ml×4). The thus obtained ethyl acetate layers containing 12a are combined, washed with a saturated aqueous solution of sodium chloride (50 ml×2) and then dried over anhydrous magnesium sulfate. After filtration and evaporation, the compound 12a partially containing racemic product is obtained as colorless needles (0.99 g, 93%). M.P. 71°–76° C. $[\alpha]_D^{20}$ −15.0° (c=2.06, acetone).

The same reaction is repeated using 8aA (M.P. 173°–175° C., $[\alpha]_D^{20}$ −154° (c=0.500, chloroform)) (388 mg, 1.43 mmole). After evaporation of the ethyl acetate extract, colorless needles (260 mg, 94%) are obtained. M.P. 88°–94° C. $[\alpha]_D^{20}$ −15.3° (c=2.08, acetone). Recrystallization from hexane-ether affords an analytical sample of 12a with an optical purity of 100% as colorless needles. M.P. 94°–96° C. $[\alpha]_D^{20}$ −16.3° (c=2.07, acetone). IR$\nu_{max}^{CHCl_3}$ cm$^{-1}$: 1718 (COOH). NMR (in CDCl$_3$ - DMSO-d$_6$): 1.80–2.10 (2H, CH$_2$C$\underline{H}_2$CCH$_2$), 2.10–3.30 (2H, m, CH$_2$C$\underline{H}_2$CCH$_2$), 2.80 (1H, d, J=16H$_z$, one of C$_6$H$_4$C$\underline{H}_2$CCOOH), 3.30 (1H, d, J=16H$_z$, one of C$_6$H$_4$C$\underline{H}_2$CCOOH), 6.55 (2H, broad s, O$\underline{H}$ and COO$\underline{H}$), 7.04 (4H, s, aromatic proton). These spectra correspond completely to those of the dl-product (M.P. 134°–135° C.: M.P. in the literature, 142°–143° C.) prepared according to the method described in the literature (A.M. El-Abbady and S. H. Doss, J. Chem. U. A. R., 8, 33 (1965)). It is proved from the result that 12a obtained from the crude 7a has an optical purity of 92% and thus the proportion of 7aA and 7aB included in the crude 7a is 96:4.

(R) (−)-2-Acetyl-1,2,3,4-tetrahydro-2-naphthol (13a)

To an ether solution (9 ml) of 12a with an optical purity of 92% (M.P. 72°–76° C., $[\alpha]_D^{20}$ −15.0° (c=1.98, acetone)) (454 mg, 2.36 mmole), an ether solution of methyl lithium (0.93 mmole/ml, 26 ml, 23.6 mmole) is dropwise added at room temperature in 1 hour and 20 minutes under stirring. After completion of the addition, the resultant mixture is stirred at room temperature for 20 minutes. The reaction mixture is then poured slowly into dilute hydrochloric acid saturated with sodium chloride (36% conc. hydrochloric acid:water=3:4) (200 ml) in 15 minutes under stirring. The dilute hydrochloric acid layer is extracted with ethyl acetate (200 ml×2). The obtained ethyl acetate layers are combined, washed with a 10% aqueous solution of sodium thiosulfate (50 ml×2) and a saturated aqueous solution of sodium chloride (50 ml×2) and dried over anhydrous magnesium sulfate. After filtration and evaporation, a pale yellow oil (453 mg) is obtained, which is purified by column chromatography (silica gel, 25 g; ether-hexane=2:1) to obtain the objective 13a with an optical purity of 92% as a colorless oil (298 mg, 67%)

([α]$_D^{20}$ −33.1° (c=3.22, chloroform)) and, as the by-product, (R) (−)-2-(2-hydroxy-2-methyl)propyl-1,2,3,4-tetrahydro-2-naphthol as colorless needles (96 mg, 20%) (M.P. 63°-65° C.; [α]$_D^{20}$ −33.3° (c=1.25, chloroform)).

13a: IR$\nu_{max}^{film}$ cm$^{-1}$: 3450 (OH), 1700 (CO). NMR (in CDCl$_3$): 1.70-2.10 (2H, m, CH$_2$CH$_2$CCH$_2$), 2.22 (3H, s, COCH$_3$), 2.40-3.10 (2H, m, CH$_2$CH$_2$CCH$_2$), 2.75 (1H, d, J=16H$_z$, one of C$_6$H$_4$CH$_2$CCOCH$_3$), 3.15 (1H, d, J=16H$_z$, one of C$_6$H$_4$CH$_2$CCOCH$_3$), 4.40 (1H, broad s, OH), 7.00 (4H, s, aromatic proton). These spectra correspond completely to those of the racemic ketone (semicarbazone, M.P. 221°-223° C.; elementary analysis: Calcd. for C$_{13}$H$_{17}$N$_3$O$_2$: C, 63.14; H, 6.93; N, 16.99. Found: C, 63.06; H, 6.95; N, 16.88) which is similarly prepared from the dl-carboxylic acid.

The alcohol as the by-product: IR$\nu_{max}^{Nujol}$ cm$^{-1}$: 3420 (OH). NMR (in CDCl$_3$): 1.23 (6H, s, CH$_3$×2), 1.50-2.15 (2H, m, CH$_2$CH$_2$CCH$_2$), 2.55 (2H, s, OH×2), 2.35-3.15 (4H, m, CH$_2$CH$_2$CCH$_2$), 7.01 (4H, s, aromatic proton).

EXAMPLE 2

Ethyl 4-(2,5-dimethoxyphenyl)butyrate

To an ethanol solution (180 ml) of 4-(2,5-dimethoxyphenyl)butyric acid (52.4 g, 0.23 mole), several drops of conc. sulfuric acid are added, and the mixture is boiled for 5 hours. After cooling in the air, a saturated aqueous solution of sodium hydrogen carbonate is added for neutralization, and the mixture is concentrated under reduced pressure. The residue is diluted with ether (300 ml), washed with a saturated aqueous solution of sodium hydrogen carbonate (50 ml×2), water (50 ml×2) and a saturated aqueous solution of sodium chloride (50 ml×1) and dried over anhydrous magnesium sulfate. After filtration and evaporation, a dark red oil (55 g) is obtained, which is subjected to distillation under reduced pressure twice for purification to obtain the objective compound as a pale yellow oil (37 g, 63%). B.P. 155°-158° C. (3 mmHg). IR$\nu_{max}^{film}$ cm$^{-1}$: 1720 (CO$_2$Et). NMR (in CDCl$_3$): 1.19 (3H, t, J=7.5H$_z$, CO$_2$CH$_2$CH$_3$), 1.56-2.06 (2H, m, CH$_2$CH$_2$CO$_2$Et), 2.06-2.46 (2H, m, CH$_2$CH$_2$CO$_2$Et), 2.46-2.76 (2H, broad t, J=6.6H$_z$, CH$_2$CH$_2$CH$_2$CO$_2$Et), 3.67 (6H, s, OCH$_3$×2), 4.15 (2H, q, J=7.5H$_z$, CO$_2$CH$_2$CH$_3$), 6.15 (3H, s, aromatic proton).

Ethyl 3,4-dihydro-5,8-dimethoxy-2-naphthoate

Sodium hydride (6.94 g, 55% oil dispersion (12.6 g), 0.289 mole) is suspended in ether (68 ml), and an ether solution (50 ml) of ethyl formate (42.8 g, 0.578 mole) is added thereto. Then, an ether solution (36 ml) containing ethyl 4-(2,5-dimethoxyphenyl)butyrate (37 g, 0.147 mole) is dropwise added in 30 minutes. The resultant mixture is stirred at 40° to 45° C. for 5 hours and then allowed to stand overnight. The reaction product solidified into a semisolid is placed into water (300 ml) under ice-cooling, and the resultant aqueous solution is extracted with ether (300 ml×2). The aqueous layer is neutralized with conc. hydrochloric acid and, after being saturated with sodium chloride, extracted with ether (300 ml×2). The obtained ether layer is dried over anhydrous magnesium sulfate and then subjected to filtration and evaporation to obtain a crude product of ethyl, 3,4-dihydro-5,8-dimethoxy-2-formylbutyrate as a red brown caramel (19.8 g, 48%). IR$\nu_{max}^{film}$ cm$^{-1}$: 1730, 1710 (CO$_2$Et), 1680 (CHO). This caramel is immediately used in the subsequent ring closure reaction.

The firstly obtained ether extract is separately washed with a saturated aqueous solution of sodium chloride (100 ml×2), dried over anhydrous magnesium sulfate and subjected to filtration and evaporation to recover ethyl 4-(2,5-dimethoxyphenyl)butyrate as a pale yellow oil (20.0 g, recovery rate, 54%).

To a mixture of 90% phosphoric acid (84 ml) and 98% sulfuric acid (17 ml), the above obtained red brown caramel (19.0 g, 70.0 mmole) is added at −10° C., and the temperature is elevated up to 0° to 10° C. under stirring. After stirring for 2 hours, the viscous reaction mixture is poured into ice-water (380 ml) and neutralized with a 40% sodium hydroxide solution (250 ml) under ice-cooling. The precipitated pale yellow oily substance is extracted with ether (200 ml×3), and the ether extracts are combined, washed with water and a saturated aqueous solution of sodium hydrogen carbonate and dried over anhydrous magnesium sulfate. After filtration and evaporation, the objective compound is obtained as a pale yellow caramel (16.4 g), which is purified by column chromatography (silica gel, 700 g; solvent, hexane-ether (4:3)) to obtain pale yellow needles (7.6 g, 43%). M.P. 74°-76° C. Recrystallization from hexane-ether affords an analytical sample as colorless needles melting at 76°-77° C. IR$\nu_{max}^{Nujol}$ cm$^{-1}$: 1680 (CO$_2$Et). NMR (in CDCl$_3$): 1.34 (3H, t, J=7.5H$_z$, CO$_2$CH$_2$CH$_3$), 2.30-3.10 (4H, m, CH$_2$CH$_2$C=), 3.77 (3H, s, OCH$_3$), 3.80 (3H, s, OCH$_3$), 4.27 (2H, q, J=7.5H$_z$, CO$_2$CH$_2$CH$_3$), 6.60 (1H, d, J=7.2H$_z$, one of aromatic protons), 6.77 (1H, d, J=7.2H$_z$, one of aromatic protons), 7.87 (1H, broad s, CH=).

Elementary analysis: Calcd. for C$_{15}$H$_{18}$O$_4$: C, 68.69; H, 6.92. Found: C, 68.72; H, 6.96.

3,4-Dihydro-5,8-dimethoxy-2-naphthoic acid (9b)

Ethyl 3,4-dihydro-5,8-dimethoxy-2-naphthoate (7.50 g, 28.6 mmole) is added to a mixture of ethanol (50 ml) and a 2 N aqueous solution of sodium hydroxide (25 ml), and the resultant mixture is boiled for 5 hours. After completion of the reaction, the reaction mixture is concentrated to the one-fourth of the amount, diluted with water (50 ml) and washed with ether (100 ml×2). The aqueous layer is made acidic with conc. hydrochloric acid, and the precipitated white solid is collected by filtration and then dried (6.50 g, 97%). M.P.<220° C. Recrystallization from ethanol affords an analytical sample of 9b as colorless needles. M.P.<220° C. IR$\nu_{max}^{Nujol}$ cm$^{-1}$: 1660 (COOH), NMR (in CDCl$_3$ - DMSO-d$_6$): 2.20-3.00 (4H, m, CH$_2$CH$_2$C=), 3.80 (3H, s, OCH$_3$), 3.82 (3H, s, OCH$_3$), 6.75 (1H, d, J=10.7H$_z$, one of aromatic protons), 6.93 (1H, d, J=10.7H$_z$, one of aromatic protons), 7.82 (1H, broad s, CH=).

Elementary analysis: Calcd. for C$_{13}$H$_{14}$O$_4$: C, 66.66; H, 6.02. Found: C, 66.95; H, 6.06.

(S) (−)-Ethyl N-(3,4-dihydro-5,8-dimethoxy-2-naphthoyl)prolinate (10b)

To a DMF solution (40 ml) containing 9b (6.24 g, 26.2 mmole) and (S) (−)-ethyl prolinate (4.20 g, 29.3 mmole), a DMF solution (40 ml) of DEPC (4.70 g, 28.8 mmole) is added, and then a DMF solution (40 ml) of triethylamine (2.65 g, 26.2 mmole) is dropwise added thereto at 0° C. in 5 minutes. The resultant mixture is stirred at 0° C. for 2 hours and then at room temperature for 48 hours in a nitrogen stream. After completion of the reaction, the reaction mixture is diluted with ethyl acetate (1.2 liters), and the ethyl acetate solution is washed with 5% hydrochloric acid (120 ml×2), water (120 ml×2), a saturated aqueous solution of sodium chloride (120 ml×2), a saturated aqueous solution of sodium hydrogen carbonate (120 ml×2), water (120 ml×2) and a saturated aqueous solution of sodium chloride (120 ml×2) in order, dried over anhydrous magnesium sulfate and subjected to filtration and evaporation to afford the crude product 10b as a pale brown caramel (10.3 g, 104%), which is purified by column chromatography (silica gel, 250 g; solvent, ether) to obtain a pure product 10b as a colorless caramel (8.3 g, 83%). $[\alpha]_D^{20}$ −10.3° (c=2.28, ethanol). $IR\nu_{max}^{film}$ cm$^{-1}$: 1730 (CO$_2$Et), 1635 (C=C), 1603 (CON). NMR (in CDCl$_3$): 1.27 (3H, t, J=7.5H$_z$, CO$_2$CH$_2$CH$_3$), 1.70–3.10 (8H, m, CH$_2$CH$_2$C= and NCH$_2$CH$_2$CH$_2$), 3.50–3.92 (2H, m, N—CH$_2$), 3.78 (6H, s, two OCH$_3$), 4.17 (2H, q, J=7.5H$_z$, CO$_2$CH$_2$CH$_3$), 4.50 (1H, m, NCHCO), 6.15 (1H, d, J=10.7H$_z$, one of aromatic protons), 6.29 (1H, d, J=10.7H$_z$, one of aromatic protons), 7.21 (1H, broad s, CH=).

(S) (−)-N-(3,4-Dihydro-5,8-dimethoxy-2-naphthoyl)proline (11b)

To an ethanol solution (40 ml) of 10b (8.20 g, 21.5 mmole), an aqueous solution (40 ml) of potassium hydroxide (85%) (1.83 g, 28.0 mmole) is dropwise added in 5 minutes, and the resultant mixture is stirred at room temperature for 5 hours. After completion of the reaction the reaction mixture is concentrated to the one-third of the amount under reduced pressure and then washed with ethyl acetate (150 ml×2). The alkaline aqueous layer is made acidic with conc. hydrochloric acid, saturated with sodium chloride and extracted with ethyl acetate (200 ml×2). The obtained ethyl acetate extracts are combined, washed with a saturated aqueous solution of sodium chloride (30 ml×2) and dried over sodium magnesium sulfate. After filtration and evaporation, a crude product 11b is obtained as colorless prisms (7.4 g, 97%). M.P. 194°–198° C. $[\alpha]_D^{20}$ −3.0° (c=3.24, 2N-NaOH). Recrystallization from ethanol affords an analytical sample of 11b as colorless prisms. M.P. 198°–200° C. $[\alpha]_D^{20}$ −3.0° (c=3.01, 2N-NaOH). $IR\nu_{max}^{Nujol}$ cm$^{-1}$: 1730 (COOH), 1630 (CON). NMR (in CDCl$_3$-DMSO-d$_6$): 1.67–2.97 (8H, m, CH$_2$CH$_2$C= and NCH$_2$CH$_2$CH$_2$), 3.37–4.97 (2H, m, N-CH$_2$), 3.76 (6H, s, OCH$_3$×2), 4.17–4.57 (1H, NCHCO$_2$), 6.73 (1H, d, J=10.7 Hz, one of aromatic protons), 6.82 (1H, d, J=10.7 Hz, one of aromatic protons), 7.14 (1H, broad s, CH=).

Elementary analysis: Calcd. for C$_{18}$H$_{21}$NO$_5$: C, 65.24; H, 6.39; N, 4.23. Found: C, 65.12; H, 6.56; N, 4.35.

Asymmetric bromolactonization of (S)(−)-N-(3,4-dihydro-5,8-dimethoxy-2-naphthoyl)-proline (11b)

To a DMF solution (30 ml) of 11b (5.00 g, 15.1 mmole) (M.P. 194°–198° C.; $[\alpha]_D^{20}$ −3.0° (c=3.24, 2N-NaOH)), a DMF solution (40 ml) of potassium t-butoxide (1.70 g, 15.1 mmole) and a DMF solution (20 ml) of NBS (5.10 g, 28.7 mmole) are added at −20° C. in a nitrogen stream. The resultant mixture is stirred at −20° C. for 2 hours and then at room temperature for 20 hours. The reaction mixture is diluted with ethyl acetate (800 ml), and the ethyl acetate solution is washed with a 5% aqueous solution of sodium hydrogen carbonate (180 ml×6), water (180 ml×6) and a saturated aqueous solution of sodium chloride (180 ml×2) in order, dried over anhydrous magnesium sulfate and subjected to filtration and evaporation to afford a crude product 7b (mixture of 7bA and 7bB) as a pale red caramel (5.44 g, 87%). The proportion of the two kinds of diastereomers (7bA and 7bB) contained in the crude product 7b is presumed to be 98.5:1.5 on the basis of the fact that the methyl ester of 12b having an optical purity of 97% is obtained therefrom. Since the crude product is unstable, it is immediately subjected to the subsequent debromination reaction. A part of the crude product 7b (150 mg) is subjected to decolorization by the use of a short column of silica gel (1.5 g; solvent, ether-hexane (4:1)) to obtain a pale yellow caramel. $[\alpha]_D^{20}$ +36.0° (c=1.38, chloroform). $IR\nu_{max}^{film}$ cm$^{-1}$: 1760 (lactone), 1672 (CON). NMR (in CDCl$_3$): 1.56–2.86 (6H, m, CH$_2$CH$_2$C(CO$_2$) and NCH$_2$CH$_2$CH$_2$), 2.86–3.26 (2H, m, CH$_2$CH$_2$C(CO$_2$)), 3.36–3.96 (2H, m, NCH$_2$), 4.26–4.76 (1H, m, NCHCO$_2$), 3.76 (3H, s, OCH$_3$), 3.81 (3H, s, OCH$_3$), 5.56 (1H, d, J=1.7 Hz, CHBr), 6.62 (1H, d, J=10 Hz, one of aromatic protons), 6.72 (1H, d, J=10.2 Hz, one of aromatic protons).

Debromination of bromolactone (7b)

To a bromobenzene solution (50 ml) of the crude product 7b (mixture of 7bA and 7bB) (5.24 g, 12.7 mmole), a bromobenzene solution (15 ml) of tri-n-butyltin hydride (14.1 g, 48.4 mmole) and a bromobenzene solution (5 ml) of AIBN (29 mg, 1.5 mole %) are added at 60° C. in an argon stream, and the resultant mixture is stirred at 60° C. for 9 hours. The pale yellow reaction mixture is concentrated under reduced pressure at a temperature of 60° C. or lower to remove bromobenzene. The residue comprising a mixture of a yellow caramel and a pale yellow oil is subjected to column chromatography (silica gel, 300 g; solvent, hexane, hexane-ether (1:1), an then ether-ethyl acetate (4:1)) to obtain a crude product 8b (mixture of 8bA and 8bB) as colorless needles (4.01 g, 95%). M.P. 169°–174° C. $[\alpha]_D^{20}$ −138° (c=0.368, chloroform). A part of the crude product 8b (2.69 g) is recrystallized from chloroform-ether to afford an analytical sample of the predominant 8bA as colorless needles (2.17 g; recovery rate, 81%). M.P. 187°–188° C. $[\alpha]_D^{20}$ −152° (c=0.424, chloroform). $IR\nu_{max}^{Nujol}$ cm$^{-1}$: 1748 (lactone), 1650 (CON). NMR (in CDCl$_3$): 1.64–2.69 (6H, m, CH$_2$CH$_2$CCH$_2$ and NCH$_2$CH$_2$CH$_2$), 2.69–3.29 (4H, m, CH$_2$CH$_2$CCH$_2$), 3.29–3.84 (2H, m, NCH$_2$), 3.71 (3H, s, OCH$_3$), 3.76 (3H, s, OCH$_3$), 4.24–4.64 (1H, m, NCHCO$_2$), 6.54 (2H, s, one of aromatic protons).

Elementary analysis: Calcd. for C$_{18}$H$_{21}$O$_5$N: C, 65.24; H, 6.39; N, 4.23. Found: C, 64.94; H, 6.33; N, 4.31.

(R)(−)-Methyl 5,8-dimethoxy-2-hydroxy-1,2,3,4-tetrahydro-2-naphthoate (methyl ester of 12b)

To a methanol solution (66 ml) of 8bA (M.P. 186°–188° C.; $[\alpha]_D^{20}$ −152° (c=0.424, chloroform)) (1.47 g, 4.44 mmole), 7.5 N hydrochloric acid (66 ml) is added, and the resultant mixture is stirred for 8 hours under boiling. The reaction mixture is concentrated to the one-third of the amount under reduced pressure, saturated with sodium chloride and extracted with ethyl acetate (100 ml×2). The ethyl acetate layers are combined, washed with water and a saturated aqueous solution of sodium chloride and dried over anhydrous magnesium sulfate. After filtration and evaporation, a mixture of 12b and the methyl ester of 12b is obtained as a pale black caramel, which is dissolved in methanol and, after addition of an ether solution of diazomethane in an excess amount, evaporated to remove methanol to obtain a crude product of methyl ester of 12b as a pale yellow caramel (1.02 g, 87%). Purification by column chromatography (silica gel, 60 g; solvent, ether-hexane (2:1)) affords the methyl ester of 12b with an optical purity of 100% as a colorless caramel (907 mg, 77%). $[\alpha]_D^{20}$ −34.5° (c=1.69, chloroform). IR$\nu_{max}^{CHCl_3}$ cm$^{-1}$: 3520 (OH), 1730 (CO$_2$Me). NMR (in CDCl$_3$): 1.99 (2H, broad t, J=6.5 Hz, CH$_2$CH$_2$CCH$_2$), 2.53–3.23 (4H, m, CH$_2$CH$_2$CCH$_2$), 2.96 (1H, s, OH), 3.78 (3H, s, OCH$_3$), 3.80 (3H, s, OCH$_3$), 3.83 (3H, s, CO$_2$CH$_3$), 6.64 (2H, s, aromatic proton).

When the crude product of 8b (mixture of 8bA and 8bB) (M.P. 169°–174° C.; $[\alpha]_D^{20}$ −138° (c=0.368, chloroform)) (447 mg, 1.35 mmole) is treated in the same manner as above, the methyl ester of 12b partially containing racemic product is obtained as a colorless caramel (248 mg, 69%). $[\alpha]_D^{20}$ −33.3° (c=1.76, chloroform). It is proved from the result that the methyl ester of 12b partially containing racemic product which is obtained from the crude 8b has an optical purity of 97% and thus the proportion of 7bA and 7bB produced in the asymmetric bromolactonization reaction is 98.5:1.5.

(R)(−)-5,8-Dimethoxy-2-hydroxy-1,2,3,4-tetrahydro-2-naphthoic acid (12b)

To a methanol solution (8 ml) of the methyl ester of 12b having an optical purity of 100% ($[\alpha]_D^{20}$ −34.5° (c=1.69, CHCl$_3$)) (820 mg, 3.08 mmole), an aqueous solution (8 ml) of potassium hydroxide (85%) (279 mg, 4.23 mmole) is added, and the resultant mixture is stirred at room temperature for 2 hours. After completion of the reaction, the reaction mixture is concentrated to the one-half of the amount under reduced pressure, diluted with a saturated aqueous solution of sodium chloride (40 ml) and washed with ethyl acetate (50 ml). The aqueous layer is adjusted to about pH 2 with conc. hydrochloric acid, saturated with sodium chloride and extracted with ethyl acetate (100 ml×2). The ethyl acetate extract is washed with a saturated aqueous solution of sodium chloride, dried over anhydrous magnesium sulfate and subjected to filtration and evaporation to obtain an almost pure product of 12b as pale blue prisms (740 mg, 96%). M.P. 117°–120° C. $[\alpha]_D^{20}$ −37.9° (c=1.01, chloroform). IR$\nu_{max}^{CHCl_3}$ cm$^{-1}$: 3600–3200 (OH, COOH), 2800–2600 (COOH), 1710 (COOH). NMR (in CDCl$_3$): 1.84–2.24 (2H, broad t, J=6 Hz, CH$_2$CH$_2$CCH$_2$), 2.64–3.24 (4H, m, CH$_2$CH$_2$CCH$_2$), 3.78 (3H, s, OCH$_3$), 3.80 (3H, s, OCH$_3$), 6.44 (2H, broad s, OH and COOH), 6.54 (2H, s, aromatic proton). Recrystallization from ether-hexane affords an analytical sample of 12b melting at 91°–93° C. $[\alpha]_D^{20}$ −39.3° (c=0.353, chloroform). Elementary analysis: Calcd. for C$_{13}$H$_{16}$O$_5$.H$_2$O: C, 57.77; H, 6.71. Found: C, 58.10; H, 6.74.

(R)(−)-2-Acetyl-5,8-dimethoxy-1,2,3,4-tetrahydro-2-naphthol (13b)

To an ether solution (15 ml) of 12b having an optical purity of 100% (M.P. 117°–120° C.; $[\alpha]_D^{20}$ −37.9° (c=1.01, chloroform)) (670 mg, 2.66 mmole), an ether solution of methyl lithium (0.84 mmole/ml, 33 ml, 28.3 mmole) is gradually added in 1 hour and 20 minutes in an argon stream. The resultant mixture is stirred at room temperature for 30 minutes. After completion of the reaction, the reaction mixture is slowly poured into dilute hydrochloric acid (conc. hydrochloric acid: water=4:30) (270 ml) under stirring, and after saturation with sodium chloride, extracted with ether (150 ml×2). The ether extracts are combined, washed with a saturated aqueous solution of sodium hydrogen carbonate (20 ml), a 10% aqueous solution of sodium thiosulfate (10 ml) and a saturated aqueous solution of sodium chloride (20 ml) in order and dried over anhydrous magnesium sulfate. After filtration and evaporation, pale yellow needles (615 mg) are obtained. Purification by column chromatography (silica gel, 60 g; ether-hexane (4:1)) affords the objective 13b having an optical purity of 100% as pale yellow needles (420 mg, 63%). M.P. 119°–126° C. $[\alpha]_D^{20}$ −47.4° (c=1.06, chloroform). The product is recrystallized from chloroform-ether to obtain an analytical sample as colorless needles. M.P. 128°–129° C. $[\alpha]_D^{20}$ −48.2° (c=0.982, chloroform). IR$\nu_{max}^{Nujol}$ cm$^{-1}$: 3480 (OH), 1700 (COCH$_3$). NMR (in CDCl$_3$): 1.87 (2H, broad t, J=6.5 Hz, CH$_2$CH$_2$CCH$_2$), 2.29 (3H, s, COCH$_3$), 2.52–3.02 (4H, m, CH$_2$CH$_2$CCH$_2$), 3.52 (1H, s, OH), 3.76 (3H, s, OCH$_3$), 3.78 (3H, s, OCH$_3$), 6.62 (2H, s, aromatic proton).

Elementary analysis: Calcd. for C$_{14}$H$_{18}$O$_4$: C, 67.18; H, 7.25. Found: C, 67.40; H, 7.26.

By column chromatography, (R)-2-(2-hydroxy-2-methyl)propyl-5,8-dimethoxy-1,2,3,4-tetrahydro-2-naphthol which is formed as the by-product in this reaction is separated as a colorless caramel (182 mg, 26%). IR$\nu_{max}^{film}$ cm$^{-1}$: 3460 (OH). NMR (in CDCl$_3$): 1.30 (3H, s, CH$_3$), 1.34 (3H, s, CH$_3$), 1.10–2.40 (2H, m, CH$_2$CH$_2$CCH$_2$), 1.91 (1H, s, OH), 2.20 (1H, s, OH), 2.50–3.00 (4H, m, CH$_2$CH$_2$CCH$_2$), 3.77 (3H, s, OCH$_3$), 3.79 (3H, s, OCH$_3$), 6.64 (2H, s, aromatic proton).

What is claimed is:

1. A process for asymmetric synthesis of optically active 2-alkanoyl-1,2,3,4-tetrahydro-2-naphthol compounds which comprises treating L-proline or the methyl or ethyl ester thereof with a carboxylic acid of the formula:

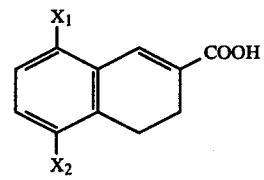

wherein X$_1$ and X$_2$ are each hydrogen or lower alkoxy in an organic solvent at a temperature from 0° C. to reflux temperature, subjecting the resulting N-($\alpha,\beta$-unsaturated acyl)-L-proline derivative of the formula:

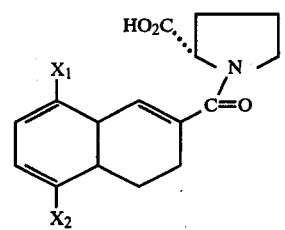

wherein X$_1$ and X$_2$ are each as defined above to asymmetric halolactonization by treatment with N- bromosuccinimide in an organic solvent at a temperature from −20° C. to room temperature, subjecting the resultant optically active halolactone of the formula:

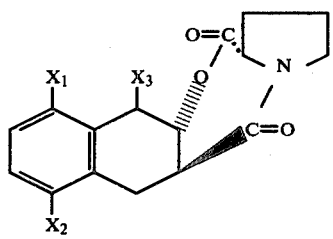

wherein $X_1$ and $X_2$ are each as defined above and $X_3$ is halogen to dehalogenation by treatment with a trialkyltin hydride in an organic solvent at a temperature from room temperature to 200° C. and then hydrolysis by treatment with water or an organic solvent at room temperature to 100° C., and treating the thus obtained optically active 2-hydroxy-1,2,3,4-tetrahydro-2-naphthoic acid of the formula:

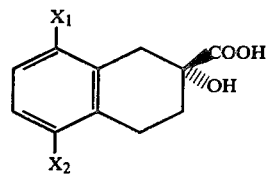

wherein $X_1$ and $X_2$ are each as defined above with an alkyl metal compound in an organic solvent at a temperature from 0° to 100° C. to obtain an optically active 2-alkanoyl-1,2,3,4-tetrahydro-2-naphthol compound of the formula:

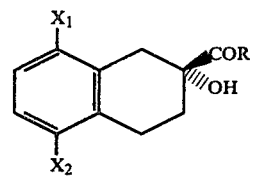

wherein $X_1$ and $X_2$ are each as defined above and R is lower alkyl.

* * * * *